United States Patent [19]
Eadington et al.

[11] Patent Number: 6,097,027
[45] Date of Patent: Aug. 1, 2000

[54] IDENTIFYING OIL COLUMNS

[75] Inventors: Peter John Eadington, East Ryde; Mark Lisk; Francis William Krieger, both of North Ryde, all of Australia

[73] Assignee: Commonwealth Scientific and Industrial Research Organisation, Campbell, Australia

[21] Appl. No.: 08/983,105

[22] PCT Filed: May 21, 1996

[86] PCT No.: PCT/AU96/00308

§ 371 Date: Apr. 29, 1998

§ 102(e) Date: Apr. 29, 1998

[87] PCT Pub. No.: WO97/04301

PCT Pub. Date: Feb. 6, 1997

[30] Foreign Application Priority Data

Jul. 20, 1995 [AU] Australia .................. PN4300

[51] Int. Cl.[7] .................................. G01N 21/64
[52] U.S. Cl. .............. 250/255; 250/301; 250/458.1; 250/459.1; 250/461.1
[58] Field of Search .................. 250/255, 301, 250/458.1, 459.1, 461.1

[56] References Cited

U.S. PATENT DOCUMENTS

| | | |
|---|---|---|
| 4,856,351 | 8/1989 | Smith . |
| 5,241,859 | 9/1993 | Smith ........................ 73/153 |
| 5,543,616 | 8/1996 | Eadington et al. ............. 250/255 |

FOREIGN PATENT DOCUMENTS

| | | |
|---|---|---|
| 344950 | 12/1989 | European Pat. Off. . |
| 414564 | 2/1991 | European Pat. Off. . |
| 415672 | 3/1991 | European Pat. Off. . |
| 465168 | 1/1992 | European Pat. Off. . |
| 2256885 | 12/1992 | United Kingdom . |

OTHER PUBLICATIONS

T. Allen "Particle Size Measurement" (Third Ed.) 1981, Chapman and Hall Ltd. (London) pp. 115–119.

Derwent Abstract No. 93–241317/30 (Gubkin Geology Inst) Jul. 23, 1992–SU 1749877.

G. Clark "The Encyclopedia of Microscopy" Reinhold Publ. Corp. (Baltimore) 1961 pp. 462–477.

*Primary Examiner*—Constantine Hannaher
*Attorney, Agent, or Firm*—Ladas & Parry

[57] ABSTRACT

A method of using natural oil inclusions in rock that is capable of oil entrapment to determine whether that rock has had, or presently contains, oil, comprising the steps of: selecting two or more regions on a sample of the rock; determining a ratio of the number of regions that contain oil inclusions, or the number of regions that do not contain oil inclusions, as against the total number of regions selected; and comparing that ratio against standard rock samples to thereby enable the determination to be made as to whether or not the rock has had or presently contains oil. The method can also be used to locate boundaries of different fluid phases in geological sites capable of retaining oil.

9 Claims, 10 Drawing Sheets

IDENTIFYING OIL COLUMNS

FIELD OF THE INVENTION

The present invention relates to method and techniques for identifying oil columns by determining whether a rock that is capable of oil entrapment has had or presently contains oil, for example, in a site suspected of containing an oil column. The invention also allows the determination of the location of various boundaries between different parts of a site, including parts that have never retained oil, parts that have previously retained oil or parts that currently retain oil. In particular, the invention makes use of two different analytical techniques (GOI and FOI; defined below) and has particular application with test drilling and exploration for oil columns, but can also be used during commercial drilling and re-exploration operations.

BACKGROUND ART

In exploration for oil columns, for example offshore (subsea) oil columns, when a potential column has been identified, (ie. using standard geological exploration techniques), it is usual practice to test-drill the site to ascertain whether the site contains oil (or could contain oil other than at the point of drilling).

Test drilling is typically expensive and is performed by stringing together pieces of pipe and drilling through, usually, a shale crust until a reservoir (eg. of sandstone or limestone) suspected of containing oil is reached. The rate of penetration of drilling increases when such a reservoir is reached, and this signifies that testing for oil in the reservoir can commence. Mud and cuttings from the drilling operation eventually reach the drill rig at the ocean surface (eg. in offshore exploration) and these are analysed in order to determine the presence or absence of oil. The techniques of cuttings analyses are collectively referred to as "shows". Known show techniques include detecting hydrocarbon gases in the mud by flame ionisation or thermal conductivity, detecting oil fluorescence by ultraviolet illumination of the mud, and oil stain, oil odour and oil cutting (adding of solvent) techniques etc. However, the existing techniques can be subject to false and/or ambiguous results. For example, heavy mud used to seal around the drill string during drilling may include hydrocarbon and this can also reach the surface during testing giving false results.

It would be advantageous if a show technique could be provided that reliably indicates oil presence (or absence) in a reservoir, either now or in the past, for example, during test-drilling and/or drill site re-exploration to assist in the location of an oil column.

SUMMARY OF INVENTION

In a first aspect the present invention provides a method of using natural oil inclusions in rock that is capable of oil entrapment to determine whether that rock has had, or presently contains, oil comprising the steps of:

(a) selecting two or more regions on a sample of the rock;
(b) determining a ratio of the number of regions that contain oil inclusion(s), or the number of regions that do not contain oil inclusion(s), as against the total number of regions selected; and
(c) comparing that ratio against standard rock samples to thereby enable the determination to be made as to whether or not the rock has had or presently contains oil.

Because the method makes use of the natural fluid inclusions within minerals in rocks that are capable of oil entrapment, it can be practiced in a highly reliable manner so that the contamination effects of other show techniques are ameliorated or eliminated. By determining a ratio in the manner as defined, and comparing that ratio against standard rock samples, the method can be standardised and, in some forms, automated so that an immediate result as to the existence or absence of oil, whether now or in the past, can be obtained (eg. in situ).

For example, when the ratio determined by the method is at or greater than a certain threshold level (eg. as determined from the standard rock samples from commercial oil columns) this can provide an indication that the sample has come from a site:

(a) of high oil saturation and currently containing an oil column with recoverable quantities of oil; or
(b) of high oil saturation some time in the past and currently not containing recoverable quantities of oil (eg. due to displacement, at some time in the past, of oil from the site either by gas or water).

The result obtained in either case can indicate that an oil column is present at the point of drilling or in the vicinity of drilling and further testing may be required to substantiate whether a commercially significant column is present.

Furthermore, in at least preferred embodiments, the ratio so yielded correlates well with actual oil saturation in the site and thus can provide a clear distinction between sites that: have never contained oil; contained oil only for a short period (ie. where the oil migrated through the site); and sites that either currently contain or have contained significant quantities of oil.

In one form of the first aspect of the invention, the regions can be two-dimensional zones of equal size, and step (a) involves selecting a known number of the zones on the sample; and step (b) involves either:
(i) counting the number of zones with oil inclusion(s) therewithin and expressing that against the known number zones to yield the ratio; or
(ii) selecting randomly a given number of zones within the known number of zones, counting the number of zones with oil inclusion(s) therewithin in the given number of zones, and expressing that against the given number of zones to yield the ratio.

This form of the invention involves a counting of the sample to determine the frequency of oil inclusions, hereinafter called "FOI", and can provide a ratio (or number) which indicates that the rock contains, contained or never contained an oil accumulation. In a most preferred application of the technique of FOI, when one of the two-dimensional zones shows one or more oil inclusions therewithin, a count of 1 only is registered (ie. the count of 1 is recorded simply when there are oil inclusion(s) within a given zone, regardless of the amount and number of those inclusions; (or alternatively where there are no inclusions within a zone a count of 1 may be recorded)).

The technique of FOI advantageously lends itself to automation as will hereinafter be explained.

In a preferred application of the technique of FOI, the rock sample can be a thin section of a larger sample of drill cuttings and/or drill core, wherein step (a) involves placing the thin section under a fluorescence microscope that is fitted with a square grid in an ocular lens thereof that divides the viewed sample into the known number of zones;

and step (b) involves activating the fluorescence microscope to radiate the sample, and counting those zones that contain fluorescing oil inclusions, either in the known number of zones or in the given number of zones.

For ease, either the given or known number of zones can be set as 100 so that the ratio can be expressed as a percentage (thereby yielding an FOI number).

The calculated FOI number for a given sample can be compared against standard rock samples to yield, for example, maximum oil saturation of the rock from which the sample has been taken. Certain values of FOI may then indicate whether the rock has had or presently contains oil, or has never contained oil, or that might suggest an adjacent oil column, etc.

When the term "standard rock sample(s)" is used in the present specification, it is a reference to rock samples with a known entrapped oil content, for example, of known oil saturation, or samples that have come from a site wherein the entrapped oil and maximum oil contents for that site are known. Oil content and oil saturation etc can be determined through laborious analytical techniques such as grinding down or breaking down of a sample to liberate entrapped oil for subsequent measurement (e.g. by sensitive and accurate quantitative organic techniques). Once determined, these standards then provide a permanent reference against which FOI (and GOI as defined below) can be compared.

The technique of FOI can be used with any rock capable of oil entrapment including sandstone, carbonate and limestone-based rocks.

In a second form of the first aspect of the invention, a technique for granular rocks can be employed whereby the oil is entrapped within the grains themselves of the rock. The grains containing oil inclusions can be determined by a technique that will hereinafter be referred to as "GOI".

Preferably then in step (a), each region is a grain within a predetermined area of the rock sample and step (b) involves quantitatively determining the total number of grains in the pre-determined area and, of those grains, the number that include oil within them, thereby yielding the ratio.

Preferably the predetermined area is a plurality of equally sized fields randomly selected from a larger number of fields designated on the sample, and step (b) involves quantitatively determining the total number of grains in each randomly selected field and summing all of them to obtain a total grain number (TGN), and also counting the number of grains with oil entrapped therewithin in each randomly selected field and summing all of those to obtain a total number of grains containing oil (NGO), and wherein the ratio may be expressed as NGO/TGN.

Thus GOI can be expressed as a percentage for the ratio of the number of grains in a sample that include oil within them (eg. NGO) to the total number of grains in the sample (eg. TGN).

The calculated GOI ratio for a given sample can, for example, be collated against standard rock samples to yield maximum oil saturation for the given sample (eg. for a sample from a suspected oil column).

Thus the method of the first aspect, in addition to determining whether there is or has been oil in a geological site, can be used in some embodiments at least as a quantitative "show". Further, the method recognises that during the crystallisation of minerals such as quartz, feldspar and calcite in a site that already has oil present therein, oil can be permanently entrapped (included) within resulting crystals (ie. during digenesis in the site).

When the terminology "geological site(s)" is used in the present specification, it is intended to include any site in which diagenetic oil inclusion can have occurred, and thus includes sites where test-drilling will usually be performed, should have been performed, or may need to be re-performed, and those which are under current oil production.

In the technique of GOI, when the rock sample is a thin section of a larger rock sample of drill cutting and/or core that is suitable for placement in a fluorescence microscope fitted with a grid pattern in an ocular lens thereof, wherein the grid pattern determines the larger number of fields designated on the sample, step (b) preferably further involves radiating the sample in the microscope with electromagnetic radiation of wavelength(s) to cause fluorescence of aromatic fractions of the oil within any grains containing the same and then counting each of NGO and TGN to yield the ratio.

Alternatively, where the predetermined area comprises an entire face of the thin section (ie. where it is suspected that the rock sample will only have a few grains with oil inclusions (typically with GOI values less than 5%)), the steps of quantitatively determining the total number of grains in the sample and the number of grains with oil therewithin preferably involve placing the thin section in a fluorescence microscope, radiating the sample with electromagnetic radiation of wavelength(s) to cause fluorescence of aromatic fractions of the oil within any grains containing the same, and then yielding the ratio by:

(i) counting the number of grains with oil therewithin in the predetermined area; and (ii) either counting the total number of grains or estimating the total number of grains.

Preferably in step (ii), the total number of grains in the predetermined area is estimated by dividing the entire predetermined area into a plurality of equally sized fields, counting the total number of grains in a pre-determined number of randomly selected fields, calculating the average number of grains per field for those fields counted, and multiplying the calculated average number of grains by the total number of equally sized fields.

For the technique of GOI, the rock sample is preferably retrieved from a granular-type rock such as sandstone-based rocks or carbonate-based rocks.

When using the preferred fluorescence microscopic techniques set forth above, electromagnetic radiation wavelengths are typically selected which induce oil fluorescence (and produce emission of visible light when the aromatic fraction of the oil fluoresces). Thus, any grains or zones having oil inclusions therewithin can be viewed and counted, and also the total number of grains or zones can be counted to yield a GOI or FOI value accordingly.

Preferably the electromagnetic radiation wavelengths include ultraviolet wavelengths of about 365 nm, and/or violet wavelengths of about 410 nm. Such wavelengths are found to produce the best emission of visible light when falling incident on the aromatic fraction of the oil inclusions. However, any wavelength of light that causes the oil inclusions to fluoresce is satisfactory.

Preferably the larger rock cutting is retrieved from a subsea, subterranean or surface outcrop geological site.

The preferred techniques of FOI and GOI are able to be conducted so that statistically reliable estimates of the occurrence of oil filled fluid inclusions in reservoir rock samples can be made.

In a second aspect the present invention provides a method for locating the position of boundaries in geological sites capable of retaining an oil column comprising the steps of:

(a) sampling in a geological site from a first rock portion capable of oil entrapment and subjecting the first rock portion sample to the technique of GOI or FOI;

(b) sampling in a geological site from one or more further and distinct rock portions, each capable of oil entrapment, and subjecting the or each further rock portion sample to the technique of GOI or FOI; and (c) comparing the results of GOI or FOI between the first rock portion and one or more of each further rock portion to determine whether or not the or each further rock portion is located in a different part of the geological site from that of the first rock portion, thereby enabling boundaries within the site to be located.

The method of the second aspect can be used on rock retrieved from sites that:

(a) have never had oil retained therein;

(b) have had oil retained therein at some point in time, but no longer retain significant and/or economical quantities of oil therein; and (c) presently retain oil therein; to determine the extent of those sites.

Preferably the geological site is located either at or near a subsea or subterranean oil column or residual oil column and sampling is performed by obtaining a cutting and/or core during drilling of the site. The terminology "residual oil column" or "residual oil zone" is used herein to refer to a site which has previously had oil retained therein at some point in time, but which no longer retains significant and/or economical quantities of oil. The terminology includes sites where a residue of oil remains (eg. former oil columns that have been displaced by water flowing into pore spaces in the rock) and sites where not even a residue of oil remains (eg. former oil columns that have been displaced by gas flowing into the pore spaces and displacing all oil in the rock). Both the techniques of FOI and GOI are such that they can detect a former oil column in a residual zone, even where there is no residue of oil.

In the method of the second aspect, when GOI is employed, the cutting and/or core is retrieved from granular-type rocks including sandstone and carbonate-based rocks, whereas when FOI is employed, the cutting and/or core is retrieved from any rocks that are capable of oil entrapment, including sandstone, carbonate and limestone-based rocks.

In some oil reservoirs there is no significant or detectable oil present in the pores of the sandstone. However, prior to the methods of the first and second aspects there was no reliable way of establishing whether the area may have previously been an oil reservoir (and thus adjacent to a reservoir which might be an actual and/or commercially significant oil reservoir). By identifying a reservoir as a residual zone, incentive may be provided for further exploration or re-exploration of an oil well site (eg. by drilling or re-drilling at adjacent lateral and/or deeper or shallower sites) which may ultimately yield commercial quantities of oil.

The method of the second aspect enables palaeo fluid contacts (ie. the boundary between different phases in a reservoir such as oil-water contact or gas-oil contact) to be identified, and thus the method may ultimately lead to the location of oil adjacent to a particular region, where previous tests would have failed to identify that the adjacent oil zone(s) might have been present. Thus, by comparing the results of GOI or FOI between one rock portion and another rock portion, it may also be possible to establish whether or not a zone is a residual zone.

BRIEF DESCRIPTION OF THE DRAWINGS

Notwithstanding any other forms which may fall within the scope of the present invention, preferred embodiments of the invention will now be described, by way of example only, with reference to examples below which refer to the accompanying drawings in which.

MODES FOR CARRYING OUT THE INVENTION

Techniques of FOI (Frequency of Oil Inclusions)

Preferred techniques of FOI were used to determine both the presence or absence of oil within various geological sites, and also boundaries between different fluid phases within those sites.

Samples from known oil zones were found to have FOI values between 39 and 98% while samples from water zones beneath the oil, which had never contained an accumulation of oil, had FOI values of between 1 and 7%.

Samples from residual oil zones, which once contained an oil accumulation, had FOI values of between 24 and 89% indicating that the FOI method recorded the highest level of oil saturation achieved irrespective of the present oil saturation.

FOI values above 10% were considered to represent a threshold for recognising oil zones and residual zones that previously contained oil.

The position of original fluid contacts (oil water contact or gas oil contact) in a well were determined by measuring FOI at intervals in a borehole and observing where the FOI value fell below 10%. This was found to be useful information in exploring and drilling for oil accumulations.

The methods aimed to record statistically reliable estimates of the frequency of occurrence of oil filled fluid inclusions in samples of reservoir rock.

Preferred FOI Methods

Sample Type: Samples of reservoir rock produced during the drilling of an oil well were used. Any type of sample was found to be satisfactory including outcrop, rotary core, cuttings, side wall core or rotary side wall core samples.

Sample Preparation: The rock sample was cut, mounted in epoxy resin and had one surface polished. This polished surface was adhered to a glass slide with the opposite surface then ground to yield a sample thickness of 0.08 mm and polished to complete preparation of the thin section.

Equipment: The thin section was observed using a microscope. Oil filled fluid inclusions were revealed by excitation with ultraviolet light (<4000 Angstom). Visual observation of fluorescence was achieved by passing emitted fluorescent light through a filter at wavelengths greater than about 4200 Angstrom.

Counting Methods: Co-ordinates were set to define a rectangular area of interest on each thin section. A computer controlled microscope stepping stage was then used to divide the area of interest into individual coterminous squares, referred to as Fields of View (FOV). Each FOV covered a 0.625 mm×0.625 mm square area so that an area of interest measuring 20 mm×10 mm would yield 512 FOV. The FOV was defined for the operator by a square grid in the ocular lens of the microscope. In a most preferred technique, one hundred of these FOV were selected at random, although some situations warranted the counting of all of the fields of view. By selecting 100 FOV, approximately 6 to 10% of the total surface area of the sample was covered. At each FOV an observation was made to determine the presence or absence of oil filled fluid inclusions within that square grid. Whilst the preferred methods involved counting zones with fluorescing oil inclusion(s), equally the count was able to be made on zones without fluorescing oil inclusions to arrive at the same result (ie. ratio or percentage).

FOI EXAMPLES

Example 1
The South Pepper Oilfield, Barrow Sub-basin, Western Australia

Samples of drill core and cuttings from four wells drilled on the South Pepper Oilfield were studied and the calculated FOI numbers are shown in Table 1.

TABLE 1

FOI Results

| Well | Depth (m kb) | Zone | Fields Counted | FOI (%) |
| --- | --- | --- | --- | --- |
| South Pepper-1 | 1220.84 | gas (relict oil zone) | 100 | 49 |
| South Pepper-1 | 1221.05 | gas (relict oil zone) | 100 | 76 |
| South Pepper-1 | 1225.3 | gas (relict oil zone) | 100 | 98 |
| South Pepper-1 | 1227.05 | gas (relict water zone) | 100 | 0 |
| South Pepper-1 | 1235.40 | oil | 100 | 62 |
| South Pepper-1 | 1245.50 | water | 100 | 7 |
| South Pepper-1 | 1260.65 | water | 100 | 3 |
| South Pepper-1 | 1280.85 | water | 100 | 0 |
| South Pepper-2 | 1241.02 | water | 100 | 0 |
| South Pepper-2 | 1252.0 | water | 100 | 0 |
| South Pepper-3 | 1247.24 | residual | 100 | 97 |
| South Pepper-3 | 1256.98 | residual | 100 | 49 |
| South Pepper-3 | 1265.70 | residual | 100 | 52 |
| South Pepper-4 | 1221.52 | gas (relict oil zone) | 100 | 41 |
| South Pepper-4 | 1225.02 | gas (relict oil zone) | 100 | 29 |
| South Pepper-4 | 1235 | oil | 100 | 44 |
| South Pepper-4 | 1241.0 | water | 100 | 1 |
| South Pepper-4 | 1245 | water | 100 | 0 |

Figure 1:
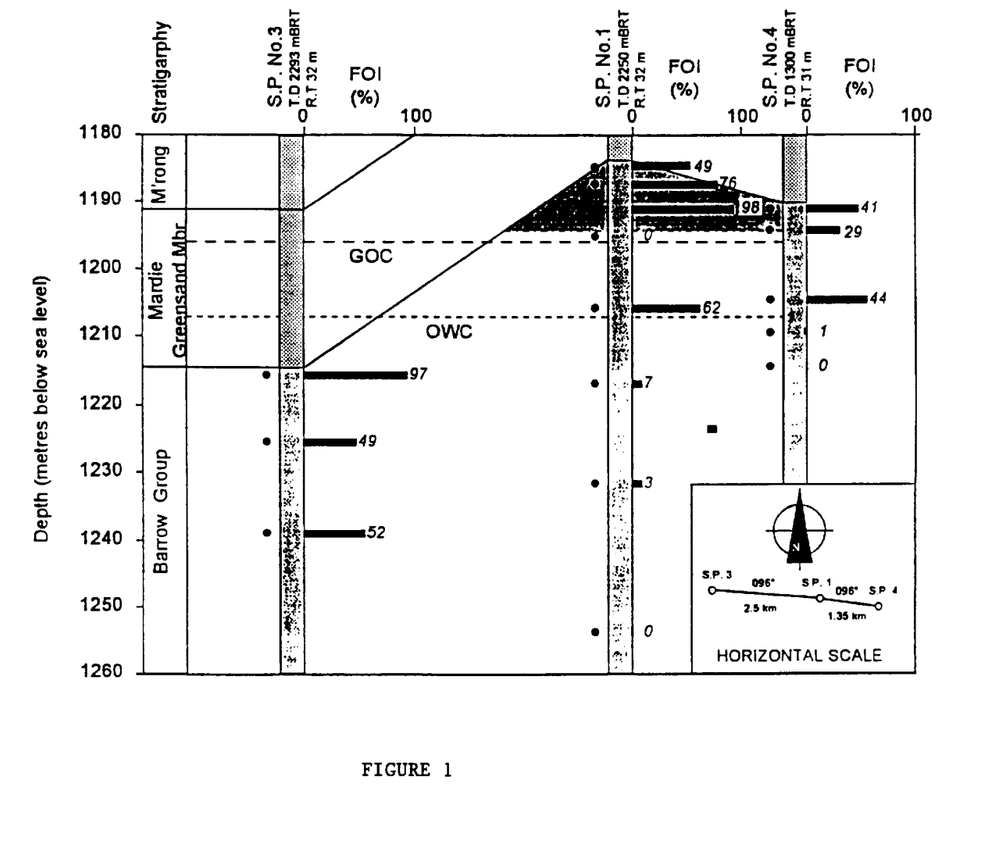
FIG. 1 shows the location of various samples and the FOI results for the South Pepper Oilfield, Barrow Sub-Basin, Western Australia.

The results are presented graphically in FIG. 1, which shows the location of samples and FOI results in the South Pepper Oilfield. The present fluid contacts (Gas-Oil and Oil-Water) are shown by dashed lines and a residual zone of high oil saturation within the gas zone is shown as the shaded region. FOI values are shown as horizontal bars on a scale from 0 to 100% at the depth from which the samples were derived.

A significant difference in FOI values was observed between samples from oil saturated rocks and samples from water bearing rocks. In addition, high FOI values recorded in presently gas bearing sand were attributed to an earlier oil accumulation while high FOI values from below the present oil-water contact (OWC) (ie. a palaeo fluid contact) in samples from the most westerly well (South Pepper-3) were observed to represent a residual oil zone. The geometry of the residual oil zone (FIG. 1) indicated that there had been late stage tilting of the trap.

The results suggested that the FOI parameter records the maximum level of oil saturation irrespective of the present fluid in the rock allowing the complete oil saturation history of an oil well to be described. FOI results from the South Pepper oilfield indicated the following hydrocarbon charge events:

1. A primary oil charge with accumulation of a small oil column with no gas cap.
2. A secondary hydrocarbon charge with accumulation of the present oil and gas column.
3. A geometric alteration of the hydrocarbon trap due to tilting of rock strata causing a subsequent modification to the palaeo fluid contacts in the field.

Example 2

A Portfolio of Oil Fields

FOI values were measured on samples from oil, water and residual zones in three oil fields from the north west shelf of Australia. All samples were sandstone reservoir rocks.

Figure 2:
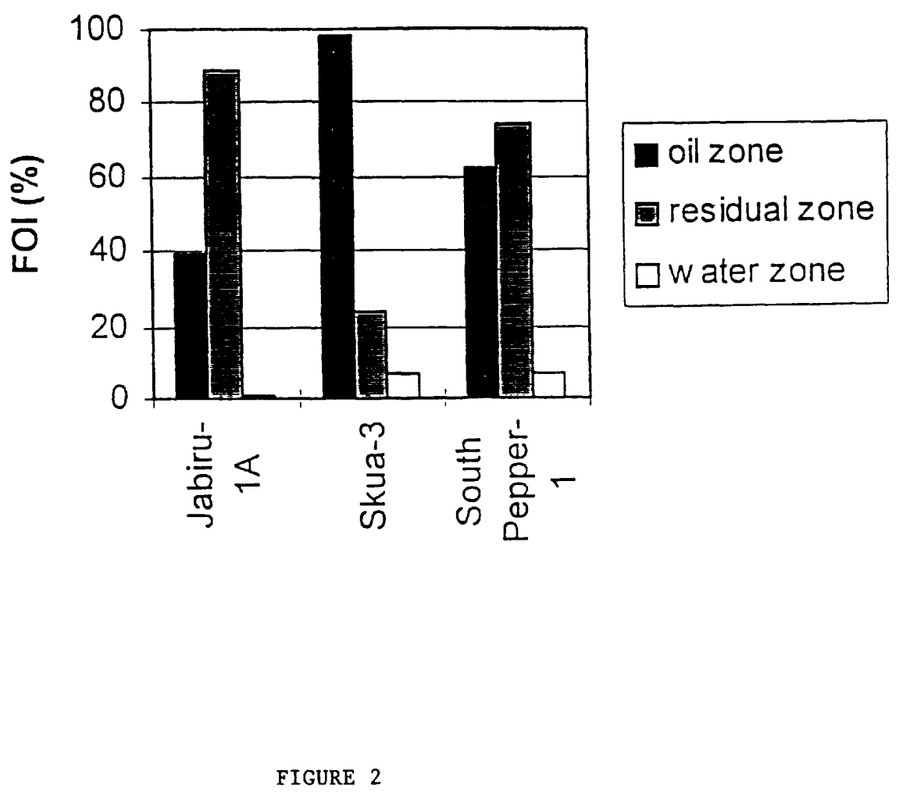
FIG. 2 shows a plot of FOI values for oil, residual and water zone samples for three different oil fields located in the North West Shelf of Australia.

Samples from the oil zones had FOI values ranging from 39 to 98% (see Table 2, and FIG. 2 which shows the FOI values from oil, residual and water zone samples for 3 oil wells). Samples from a water zone situated a long way below the oil accumulations had FOI values from 1 to 7%. Samples from directly beneath the present OWC, but interpreted to be residual oil zones had FOI values from 24 to 89%.

TABLE 2

FOI Values Recorded on Samples from Oil Zone, Residual Zone and Water Zone for 3 Producing Oil Wells

| Well | Oil Zone | Residual Zone | Water Zone |
| --- | --- | --- | --- |
| Jabiru-1A | 39 | 89 | 1 |
| Skua-3 | 98 | 24 | 7 |
| South Pepper-1 | 62 | 49 | 7 |

Statistical Validity

Samples from the Jabiru-1A well were investigated in order to test the statistical validity of the FOI technique. FOI values calculated at the completion of each field (progressive FOI Values) are shown for the 100 fields investigated in each sample (Table 3, and in FIGS. 3 to 5).

The maximum deviations from the mean (error limit) for a progressive calculation of FOI through 100 fields were ±172% of the mean value when up to 35 fields had been completed decreasing to ±6% of the mean value when more than 75 fields had been completed. Variation of ±10% of the mean value was observed to be acceptable for the geological application of the technique suggesting that the investigation of 100 fields per samples was appropriate.

TABLE 3

Variation in FOI with Increasing Field Number

| Well | Zone | Max Variation Fields 0–35 | Max Variation Fields 75–100 |
|---|---|---|---|
| Jabiru-1A | Oil | 100 | 6 |
| | Residual | 100 | 1 |
| | Water | 172 | 1 |

Figure 3:
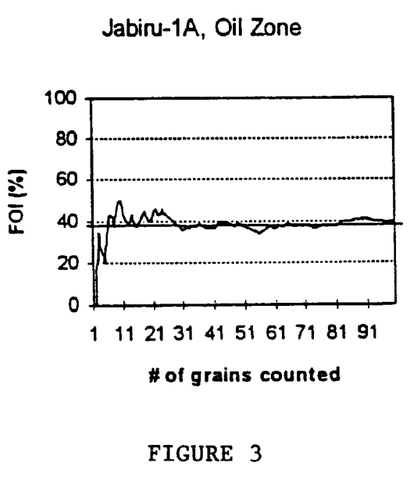
FIGS. 3, 4 and 5 are three different graphs showing the variation in FOI for samples from oil, residual and water zones in oil field Jabiru-1A, showing the effect on FOI with an increasing number of fields counted.
Figure 4:
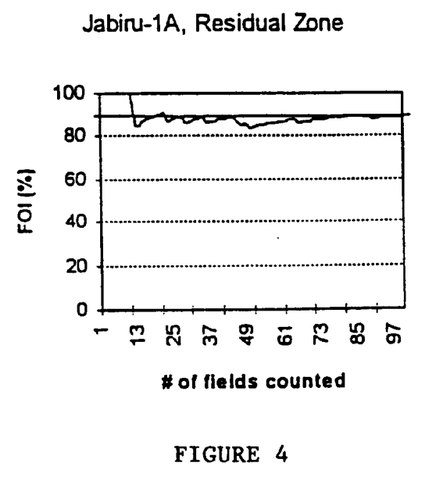
Figure 5:
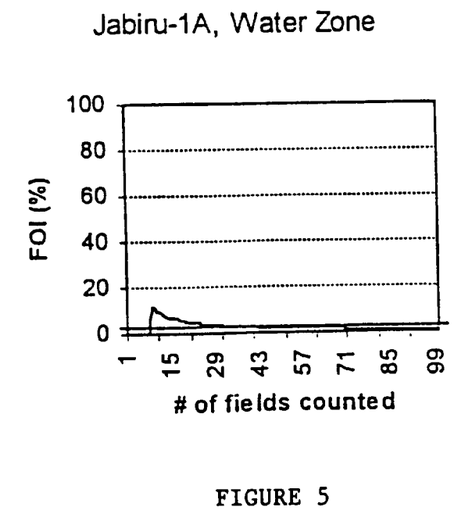

FIGS. 3 and 4 are graphs showing the variation in FOI with increasing number of fields investigated (Progressive FOI Values) for samples from oil, residual and water zones respectively in Jabiru-1A. The overall mean is also shown.

A significant difference in FOI was observed to exist between oil zone samples and water zone samples. The FOI is also high in residual zones, that is, rocks that once had a high oil saturation but are now water wet due to loss of oil. This is because the FOI number records the frequency of oil inclusions and these inclusions, once formed, are retained as a permanent record and indicate that the rock previously had a high oil saturation.

Example 3

Applications

In oil exploration, the FOI count provided a conclusive assessment of whether the maximum oil saturation experienced by a rock was consistent with an oil accumulation. This reflected either high oil saturation at the present day or at some time in the geological past. Knowledge that a well had intersected a zone of high oil saturation had implications for future investigation (irrespective of whether that high oil saturation exists at the present day).

Figure 6:
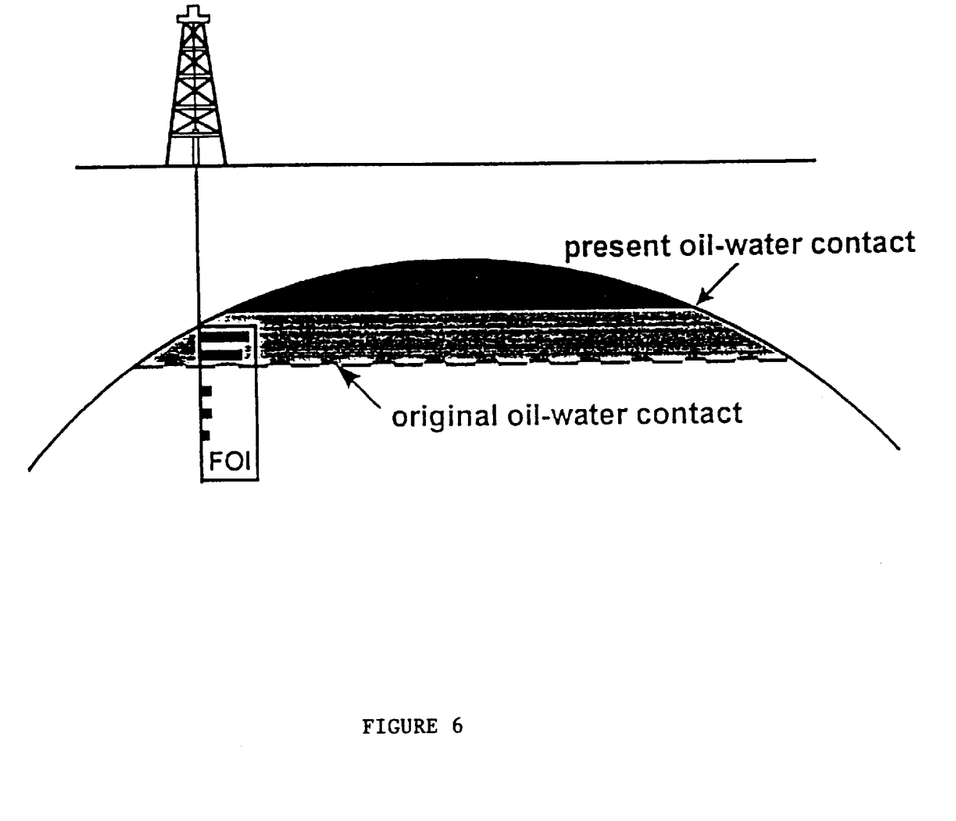
FIG. 6 shows schematically how FOI can be used to map original oil-water contacts.

As FOI relies on oil inclusions which are enclosed in minerals (mainly quartz, feldspar and carbonate minerals), the FOI value is, consequently, permanently preserved as an indicator of the highest level of oil saturation. The change from high FOI to low FOI was therefore used to map original fluid contacts, as shown schematically in FIG. 6 and this information was seen to be valuable for evaluating a range of geological scenarios.

Figure 7:
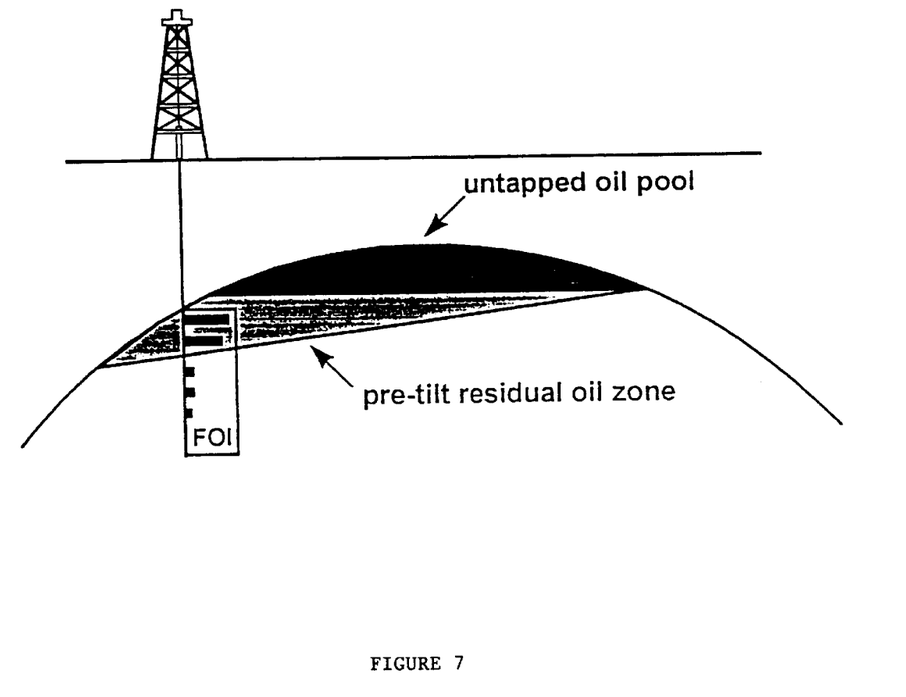
FIG. 7 shows how FOI can be used to show a residual zone underlying an oil zone.

As shown schematically in FIG. 7, FOI can be used to identify residual zones, (rocks that previously had a high oil saturation). A residual zone identified in a drill hole that is now water wet indicated there was an oil accumulation that had decreased in size, (ie. the oil water contact had moved upwards) indicating potential for a current oil accumulation in rocks higher in the reservoir.

Figure 8:
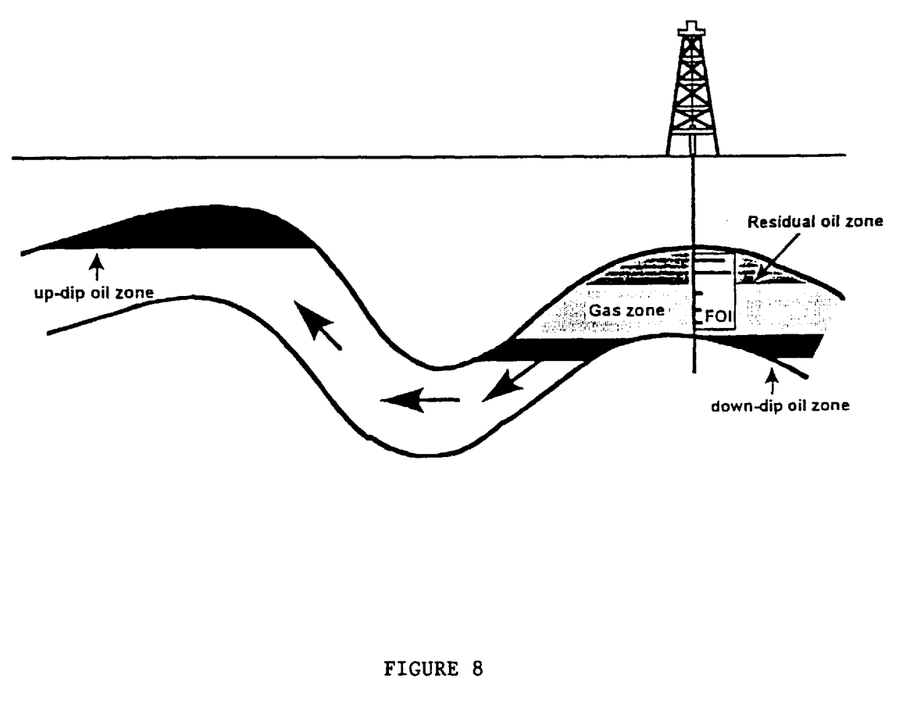
FIG. 8 shows how FOI can detect a residual zone that has been formed when gas displaces oil in that zone.

As shown schematically in FIG. 8, a residual zone within a gas column indicated that oil may have been displaced downwards (down-dip) and may now reside as an oil column beneath the gas (ie. displaced by the gas). Alternatively, oil may have been displaced to a high structure (up-dip).

Figure 9:
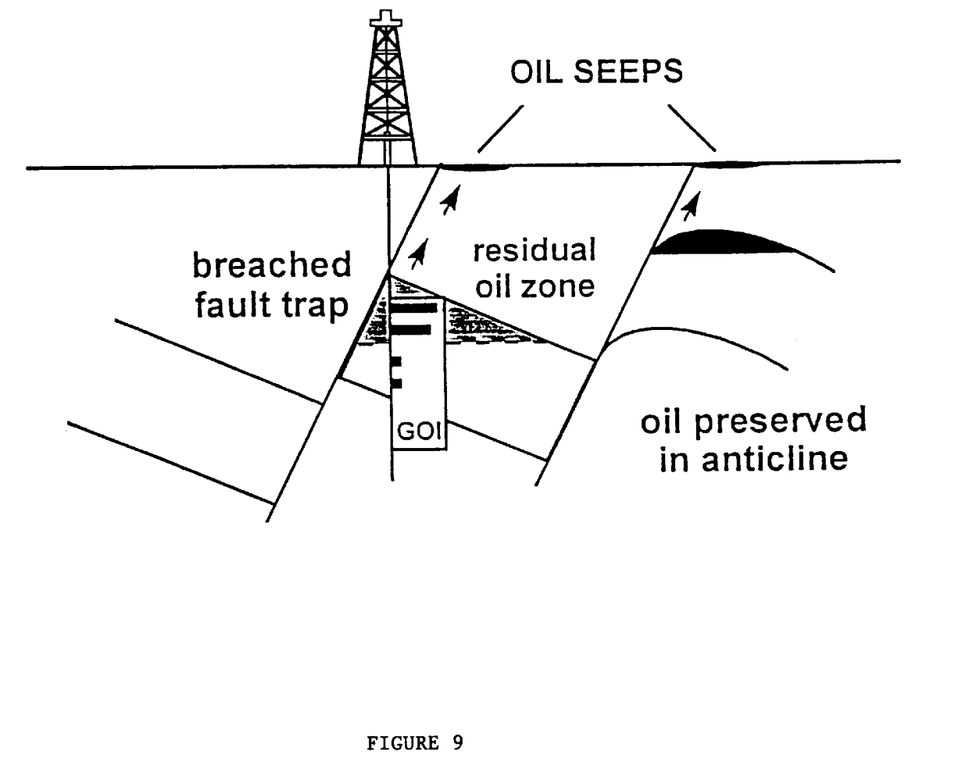
FIG. 9 shows how FOI can be used to evaluate different oil trap types.

FIG. 9 shows schematically how FOI can be used to evaluate different trap types. A residual zone identified in a drill hole that is now water wet indicated a problem with that particular type of hydrocarbon trap (ie. a trap relying on a fault for its seal). New drilling targets then focussed on traps such as anticlines which do not rely on the sealing capacity of faults.

FINDINGS

It was accordingly observed that the FOI technique:
measured the frequency of oil inclusions;
differed significantly between samples from oil zones and samples from water zones;
relied on oil inclusions which were permanently sealed in minerals with a framework structure and consequently high FOI was preserved as an indicator of relict oil zones;
allowed original fluid contacts (oil-water or gas-oil) to be located as the place where FOI decreased sharply from high to low values;
allowed for automation of the counting process, because only fields needed to be counted and not individual grains or inclusions.

Techniques of GOI (Grains containing Oil Inclusions)

Preferred techniques of GOI were used to determine both the presence or absence of oil within particular zones and the location of boundaries between particular zones in a number of different geological sites. The techniques were found to be useful in establishing the location of residual zones, (which subsequently could lead to the location of an oil zone). It was generally determined that samples from existing oil-producing and residual zones had GOI values between 5% and 70%. GOI as a percentage was established according to the following equation:

$$GOI(\%) \; NGO/TGN \times 100/1(\%)$$

where GOI=grains containing oil inclusions, NGO=the number of grains with oil included therein and TGN=the total number of grains in a sample.

It was also determined that 5% was a threshold GOI value in recognising both oil zones and residual (GOI) zones, and that zones which had never contained or had an accumulation of oil (eg. subsea rock formations permeated by water) had GOI values less than 1%.

The technique was observed to be useful in establishing the location of palaeo fluid contacts such as oil-water contact boundaries, gas-oil contact boundaries etc. These contacts were established when measuring GOI values at different intervals in a borehole formed during test and commercial drilling, and observing where in the borehole the GOI value decreased from a high value (ie. greater than 5%) to a low value (ie. less than 1%). In general, the information derived from GOI analyses was found to be very useful information in all types of oil exploration and drilling.

Preferred GOI Methods

Samples of reservoir rock from various Australian offshore test drill sites (ie. resulting from the test drilling operation) were retrieved. Satisfactory samples included rotary core, cuttings such as ditch cuttings, side wall core and rotary side wall core samples.

The samples were then cut, ground and polished to produce a thin section (usually 0.08 mm thick) for mounting on a glass slide and so as to present a polished upper surface with no cover glass. Core samples were impregnated with epoxy prior to preparation, whereas cutting samples were dispersed in epoxy prior to preparation.

Typically, the glass slides were then mounted in a fluorescence microscope capable of irradiating both UV and violet light. Where the samples were from a sandstone reservoir, sand grains were typically observed to be 0.05 to 1 mm in diameter. The technique of dark field fluorescence microscopy was employed. In this method, the oil filled fluid inclusions were revealed by excitation with ultraviolet light of about 365 nm and violet light of about 410 nm (ie. typically light of less than 4000 Angstrom) and then the fluorescent light resulting from excitation of the aromatic fractions of the oil was observed through a filter at wavelengths greater than about 4200 Angstrom (ie. emission spectra ranging from yellow (about 550 nm) to blue (about 440 nm)).

An autoscan microscope stage was then used to position the sample on the microscope by robotic motor action under computer control. The sample was examined with a 10× objective lens and a square 10×10 grid in the ocular lens that overlay an area of (0.625 mm×0.625 mm) on the sample. A sample on a glass slide lens had an area of about (20×30) mm² which enabled the positioning of, usually, a 1400 grid overlay thereover (ie. having 1400 positions, or hereinafter "fields") for complete inspection. Collectively, the coterminous fields formed a rectangular area that covered as much of the thin section as possible, and all of this area could be examined by moving the sample in traverses by a step distance equal to the size of the grid in the ocular lens.

A limited sample of fields (eg. 100) was selected for counting from the possible 1400 fields, this sample being selected at random using the computer commanding the autoscan positioner. Sample irradiation was then commenced. Using the square grid in the ocular lens of the microscope as a guide, the total number of grains were counted as were the number of grains containing oil inclusions in each selected field.

An unbiased estimate of the total number of grains in a sample was obtained by counting whole grains that lay within the grid or that crossed two adjacent edges of the grid or the corner therebetween. Grains that crossed the other two edges or the three associated corners of the grid were not counted. [This method avoided bias due to grains crossing the edge of the grid and avoided potential errors that might arise in estimating fractions of grains across the edge of the grid or double counting if whole grains across all four edges of the grid were counted].

In the technique, the sample appeared generally dark, and bright lights appeared where there was fluorescence. GOI was then computed as the number of grains containing oil inclusions summed for the 100 fields as a percentage of the total number of grains also summed for the 100 fields.

The identification and interpretation of residual oil zones was also possible in situ (ie. whilst drilling) when the GOI values were directly turned into a graph on a geophysical, electric or lithologic log of the borehole.

STATISTICAL VALIDITY

To check the statistical validity of the GOI testing and also to expand on the ranges of application of the GOI technique, two methods were used to obtain a statistically meaningful GOI determination.

Method (1)

Samples with a high proportion of grains containing oil inclusions, which typically had GOI values greater than 5%, were counted at a number of fields selected at random from the total number of field locations. Typically in testing there were 1000–1500 fields and at each field the total number of grains and the total number of grains containing oil inclusions were counted. As indicated above, the GOI was usefully calculated from the aggregate counts for 100 fields.

Figure 11:
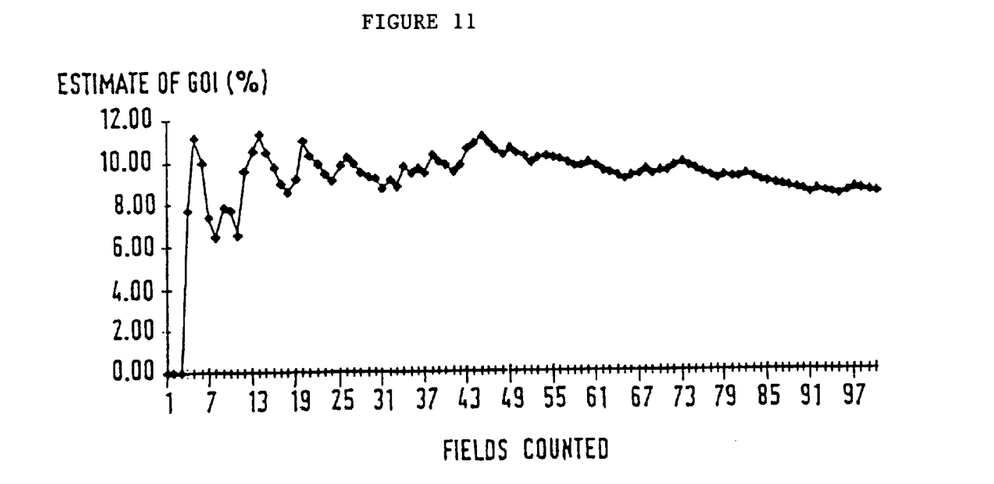
FIG. 11 shows a plot of progressive GOI values indicating how sampling error can be reduced when a preferred method (1) of establishing GOI (below) is followed.

The statistical validity of the method was checked by plotting a graph of the aggregate GOI for the 100 fields in a progressive manner. The results of this graph are shown in FIG. 11. Progressive GOI values were found to fluctuate within limits that decreased from ±78% with less than 35 fields counted to ±11% when more than 75 fields were counted.

Method (2)

Samples with a low proportion of grains containing oil inclusions, which typically had GOI values less than 5%, were counted by observing every field on the thin section to obtain the total number of grains containing oil filled fluid inclusions.

An estimate of the total number of grains in the section was made by counting the number of grains at 35 randomly selected fields and multiplying the average number of grains per field by the total number of fields on the sample. GOI was then calculated as the ratio of the total number of grains containing oil filled fluid inclusions divided by the estimate of the total number of grains.

Figure 12:
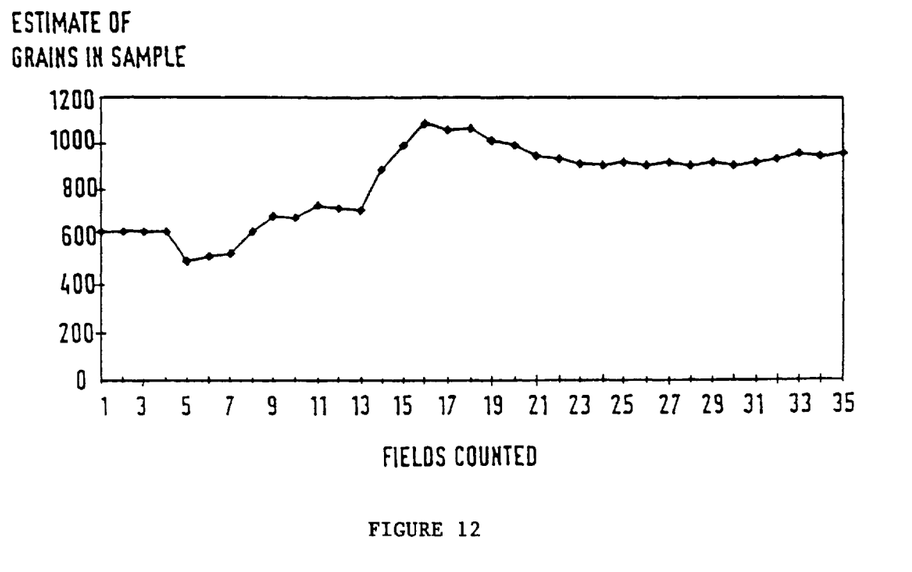
FIG. 12 shows a plot of the progressive estimates of the total number of grains in a thin section sample and how error can be reduced when a preferred method (2) of calculating GOI (below) is followed.

The statistical validity of the estimate of the total number of grains was checked by plotting the progressive estimate of the number of grains for the 35 random fields. The results of this plot are shown in FIG. 12. The progressive estimate was found to fluctuate within limits that decreased from ±48% for less than 20 fields to ±4% for more than 25 fields.

GOI EXAMPLES

Example (4)

Preferred Calculation of GOI in the Talisman 1 Oilfield, Dampier Basin, Western Australia Samples of drill cuttings from two oil columns in the Talisman 1 reservoir, one above the other, were counted. The upper oil column was contained within the A sand (see FIG. 10) and there was determined to be an oil-water contact at 1923.5 m below the rotary table (mrt). A lower oil column was found to be contained within B and C sands (FIG. 10) and an oil-water contact was located at 1971.5 mrt.

The results of GOI were then presented in Table 4 (below). The oil zone sample from the upper oil column was found to have a GOI of 8.4% and the water zone sample from below the oil-water contact was found to have a GOI of 0.2%. Two oil zone samples from the lower oil column were found to have GOI values of 5% and 9.4% respectively and three water zone samples from below the oil-water contact were found to have GOI values of 0.3%, 0.7% and 0.9% respectively.

TABLE 4

GOI Results in the Talisman 1 Oilfield

| Depth (mkb) | Formation | GOI (%) | Total Grains Counted | Total Grains Oil incls |
|---|---|---|---|---|
| 1915–20 | 'A' sand oil zone | 8.4 | 451 | 38 |
| 1925–30 | 'A' sand water zone | 0.2 | 958 | 2 |
| 1945–50 | | 5.0 | 261 | 13 |
| 1959–62 | 'B' sand oil zone | 9.4 | 330 | 31 |
| 1974–77 | 'C' sand oil zone | 0.9 | 2498 | 23 |
| 1986–89 | 'C' sand water | 0.7 | 2826 | 20 |
| 1995–98 | 'C' sand water 'D' sand water | 0.3 | 2042 | 6 |

It can be seen that the difference in GOI values between samples from oil saturated rocks and samples with no oil saturation differed by approximately one order of magnitude. That is to say values ranging from about 5% to 10% in the oil zone were found whereas values ranging from about 0.3% to 1% in the water zone were found.

Figure 10:
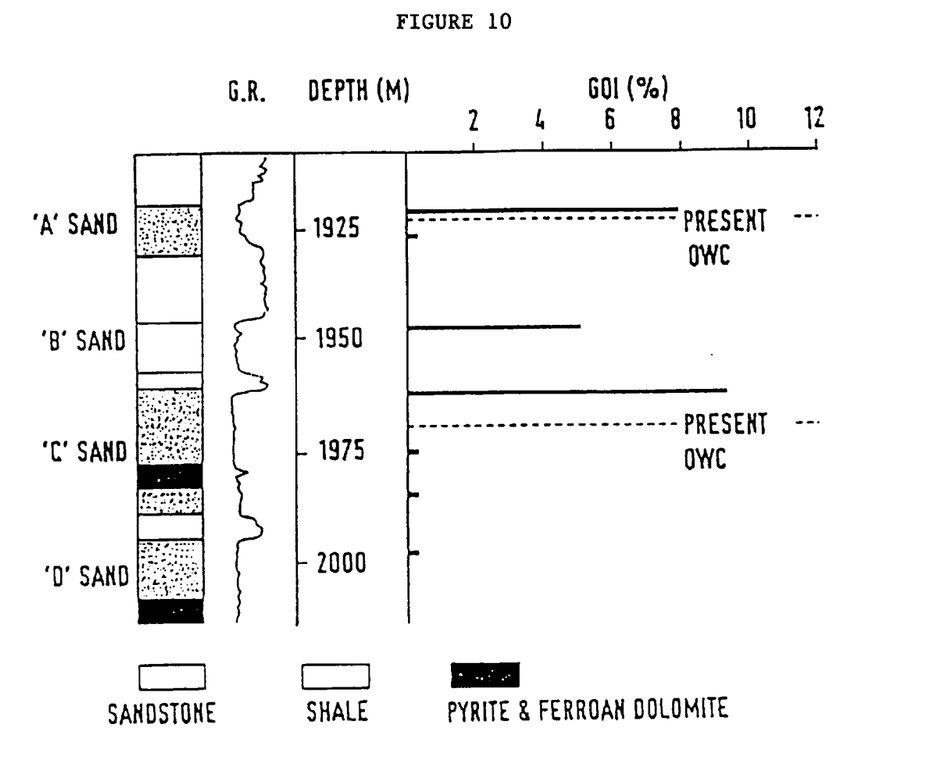
FIG. 10 shows the location of various rock samples and the GOI results for an oilfield in the Dampier Basin, Western Australia.

FIG. 10 graphically presents the results of GOI analysis in the Talisman 1 oilfield. FIG. 10 also includes a lithology log (column 1), a gamma ray log (column 2), and designated G.R., and a depth scale (column 3) to show the various depths of the different zones within the geological sites. GOI values are shown as horizontal bars on a scale from 0% to 12% at the depth from which the samples were derived.

The permeable reservoir rocks were revealed on the gamma ray trace as intervals of relatively low gamma ray count and were represented as a stippled pattern on the lithology log. The intervening shale seal rocks were intervals with relatively high gamma ray count and were shown without pattern on the lithology log. The current contacts between oil and water were shown as dashed horizontal lines.

Example 5
GOI Portfolio of Various Australian Oilfields

Figure 13:
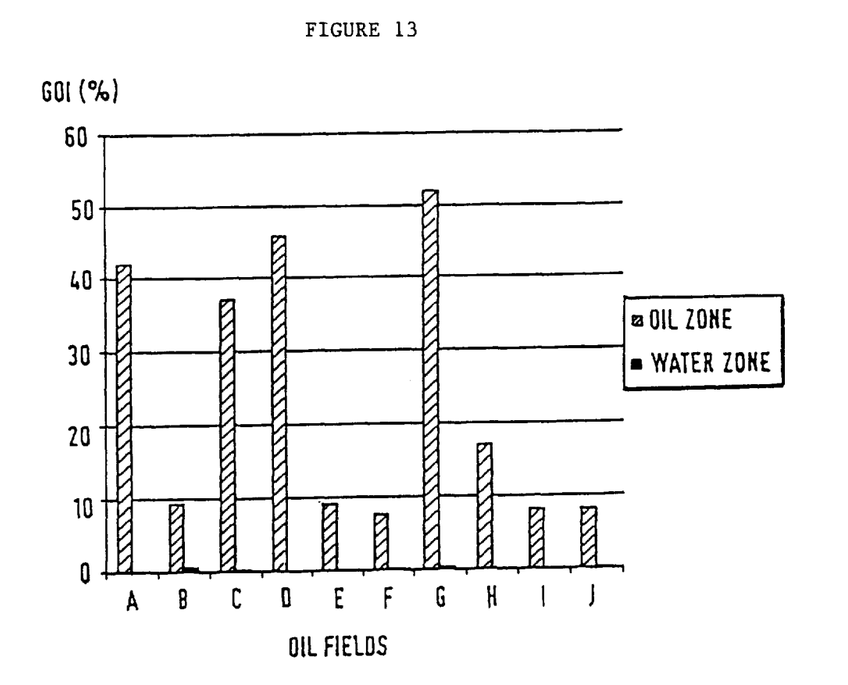
FIG. 13 plots the results of a preferred GOI test in ten different subsea oilfields located off the north-west shelf of Australia.

GOI was measured in ten oilfields in the north-west shelf of Australia. Samples from the oilfields included potentially oil-containing sandstone reservoir rocks. The ten oilfields were designated as A through to J and the results were presented in Table 5 and graphically in FIG. 13.

Samples from the oil zones were found to have GOI values from 9% to 52%. Samples from the water zone below the oil accumulations were found to have GOI values from 0% to 0.7%.

Some of those zones were observed as having a residual (GOI) zone below with an elevated GOI indicating that the reservoir had been filled with oil to the base of the reservoir rock. In such cases, a palaeo oil-water contact could not be delineated and so the annotation "residual" was deemed to be appropriate (see Table 5).

TABLE 5

GOI Values from Oil Zone and Water Zone

|  | Oil Zone | Water Zone |
| --- | --- | --- |
| Field A | 42 | Residual |
| Field B | 9.4 | 0.7 |
| Field C | 37 | 0.3 |
| Field D | 46.0 | Residual |
| Field E | 9.1 | Residual |
| Field F | 7.7 | 0.2 |
| Field G | 52.0 | 0.5 |
| Field H | 17.0 | 0.0 |
| Field I | 8.2 | Residual |
| Field J | 8.2 | 0.2 |

Figure 14:
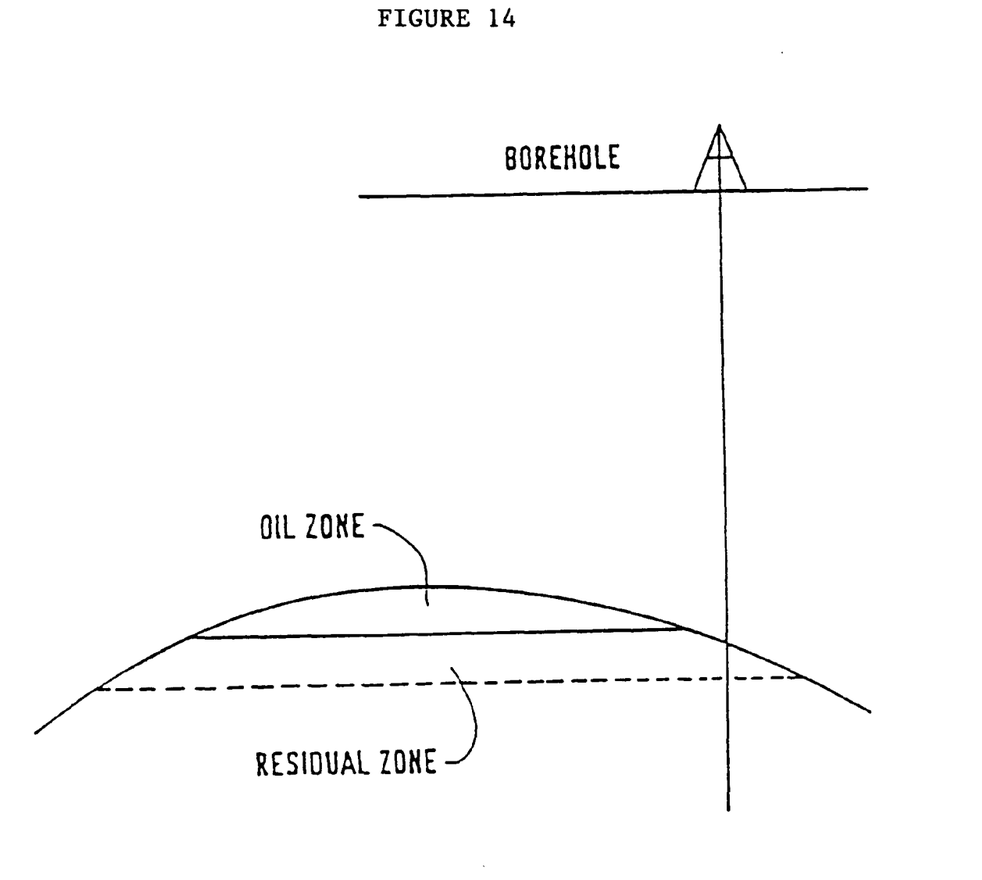
FIG. 14 shows a schematic illustration in cross-section of a potential oil well site showing how a drilling operation (borehole) can locate a residual (GOI) zone only, when an oil zone is in close proximity.

Referring to the schematic representation of FIG. 14 it can be seen how a residual (GOI) zone may underlie an oil zone and how the oil zone may be missed if the borehole is drilled at an inappropriate place and ambiguous or negative "oil show" test results are received. GOI can be used to identify the residual (GOI) zone so that a now water wet zone might indicate that there is an oil accumulation somewhere above this zone (eg. where the oil accumulation has decreased in size through leakage etc). Alternatively, GOI with other testing may identify a residual zone within a gas column, indicating that oil may have been displaced downwardly and may now reside as an oil column beneath the gas.

FINDINGS

It was found that there was a significant difference in GOI between oil zone samples and water zone samples. The difference was found to be approximately one order of magnitude. GOI was also found to be high in residual (GOI) zones (typically rocks that once had a high oil saturation but were now water wet due to loss of oil). The accuracy in the discovery of oil zones (including residual (GOI) zones) was attributable to the technique of GOI, because GOI counting was always made on grains containing oil inclusions which, once formed, were known to be permanent records of the rock that previously had a high oil saturation.

CONCLUSIONS

It was determined that GOI and FOI techniques can be reliably used in oil exploration to determine whether a rock has had an oil accumulation at some stage or has never had an oil accumulation and also can be used as an adjunct to current procedures for testing for the presence of oil accumulation. The techniques can also be used to identify rocks that have not had high oil saturation, to screen rocks prior to testing (eg. prior to an expensive drill stem test) and by identifying and removing from contention those rocks that have never had an oil accumulation. Also, by knowing that rocks once contained oil provides information that ambiguous results from other forms of testing for oil are to be questioned, and that repeat testing or supplementation with alternative tests to obtain a definitive result should ensue.

The GOI and FOI techniques were found to be particularly applicable to subsea reservoirs, but could also be applicable to subterranean (ie. underground reservoirs on land), and particularly in the case of FOI, to a wide variety of rock types. FOI could also be readily automated.

While the invention has been described with reference to a number of preferred embodiments it should be appreciated that the invention can be embodied in many other forms.

What is claimed is:

1. A method of using natural oil inclusions in rock that is capable of oil entrapment to determine whether that rock has had or presently contains oil, the method comprising the steps of:
    (a) selecting two or more two-dimensional zones of equal size on a sample of the rock to yield a known number of zones;
    (b) determining a ratio of the number of zones that contain oil inclusion(s), or the number of zones that do not contain oil inclusion(s), as against the known number of zones selected, either by:
        (i) counting the number of ones with oil inclusion(s) therewithin and expressing that against the known number zones to yield a ratio; or
        (ii) selecting randomly a given number of zones within the known number of zones, counting the number of zones with oil inclusion(s) therewithin in the given number of zones, and expressing that against the given number of zones to yield a ratio; and
    (c) comparing that ratio against standard rock samples to thereby enable the determination to be made as to whether or not the rock has had or presently contains oil.

2. A method as claimed in claim 1, wherein the rock sample is a thin section of a larger rock cutting and/or core, and step (a) involves placing the thin section under a fluorescence microscope that is fitted with a square grid in an ocular lens thereof that divides the viewed sample into the known number of zones;

and step (b) involves activating the fluorescence microscope to radiate the sample, and counting those zones that contain fluorescing oil inclusions, either in the known number of zones or in the given number of zones.

3. A method as claimed in claim 2, wherein the fluorescence microscope emits electromagnetic radiation wavelength(s) including ultraviolet wavelengths of about 365 nm, and/or violet wavelengths of about 410 nm.

4. A method as claimed in claim 2, wherein the larger rock cutting and/or core is retrieved from either a subsea, subterranean or surface outcrop geological site.

5. A method as claimed in claim 1 or 2, wherein either the given number or known number of zones is set as 100 so that the ratio can readily be expressed as a percentage.

6. A method as claimed in claims 1 to 2, wherein the rock sample is retrieved from any rock capable of oil entrapment including sandstone-based rocks, carbonate-based rocks, and/or limestone-based rocks.

7. A method for locating the position of boundaries in geological sites capable of retaining an oil column comprising the steps of:

(a) sampling in a geological site from a first rock portion capable of oil entrapment and subjecting the first rock portion sample to the technique of FOI;

(b) sampling in a geological site from one or more further and distinct rock portions, each capable of oil entrapment, and subjecting the or each further rock portion sample to the technique of FOI; and (c) comparing the results of FOI between the first rock portion and one or more of each further rock portion to determine whether or not the or each further rock portion is located in a different part of the geological site from that of the first rock portion, thereby enabling boundaries within the site to be located.

8. A method as claimed in claim 7, wherein the geological site is located either at or near a subsea or subterranean oil column or residual oil column, and sampling is performed by obtaining a cutting and/or core during drilling of the site, thereby enabling the boundaries of either column to be located.

9. A method as claimed in claim 8, wherein the cutting and/or core is retrieved from any rock capable of oil entrapment including sandstone-based rocks, carbonate-based rocks, and/or limestone-based rocks.

\* \* \* \* \*